United States Patent [19]

Helman et al.

[11] Patent Number: 5,028,418

[45] Date of Patent: Jul. 2, 1991

[54] ANTIPERSPIRANT PROCESS AND IMDAZOLE CONTAINING COMPOSITIONS UTILIZABLE THEREIN

[75] Inventors: Michael D. Helman, Edison; Thomas A. Re, Hazlet, both of N.J.

[73] Assignee: Bristol-Myers Squibb Company, New York, N.Y.

[21] Appl. No.: 495,179

[22] Filed: Mar. 19, 1990

[51] Int. Cl.$^5$ .......................... A61K 7/32; A61K 9/10; A61K 9/12; A61K 9/14
[52] U.S. Cl. ........................................ 424/65; 424/47; 424/69; 514/858; 514/860; 514/937; 514/938; 514/939
[58] Field of Search ........................................... 424/65

[56] References Cited

U.S. PATENT DOCUMENTS 4,737,361 4/1988 Raft et al. ........................... 424/65
4,741,899 5/1988 Henry et al. ........................ 424/65

FOREIGN PATENT DOCUMENTS 0273202 7/1988 European Pat. Off. .............. 424/65

OTHER PUBLICATIONS

Merck Index, 1976, Ninth Edition, 3472.

*Primary Examiner*—Dale R. Ore
*Attorney, Agent, or Firm*—Morton S. Simon

[57] ABSTRACT

Perspiration is decreased in an area of the skin subject to perspiration by applying to such area an antiperspirant amount of an imidazole derivative of the formula I

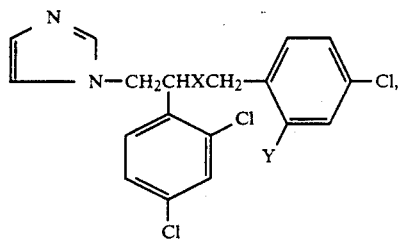

wherein X is O or S and Y is Cl or H, or a dermatologically acceptable salt thereof, preferably in a dermatologically acceptable compatible vehicle.

24 Claims, No Drawings

ANTIPERSPIRANT PROCESS AND IMDAZOLE CONTAINING COMPOSITIONS UTILIZABLE THEREIN

FIELD OF INVENTION

This invention relates to an antiperspirant process and compositions utilizable therein. More particularly, it relates to antiperspirant compositions containing an antiperspirant amount of certain imidazole derivatives. Such derivatives include miconazole, econazole and sulconazole.

BACKGROUND OF INVENTION

Four topical antiperspirants have been classified by the United States Food & Drug administration advisory review panel as safe and effective when used in the appropriate concentration. These include aluminum chloride, aluminum chlorohydrates, buffered aluminum sulfate and aluminum zirconium chlorohydrates.

There is a need for new and effective antiperspirants and antiperspirant compositions, particularly those having a proven record of long term safety.

Miconazole, an imidazole derivative having the structure

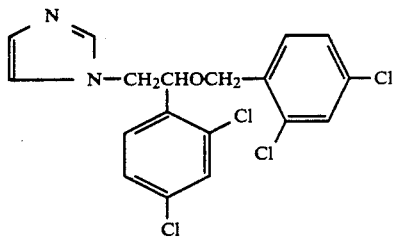

is a well known safe and effective topical antifungal. For such purposes Miconazole is generally employed as the nitrate salt. Miconazole nitrate is commercially available as a 2% dermatological cream, spray, powder or lotion.

Econazole, another imidazole derivative having the structure

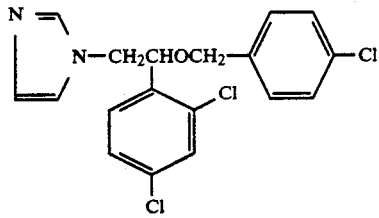

is another safe and effective topical antifungal agent. It is generally employed as the mononitrate salt and is commercially available as a 1% cream.

Sulconazole, is yet another safe and effective topical antifungal imidazole derivative. It has the structure:

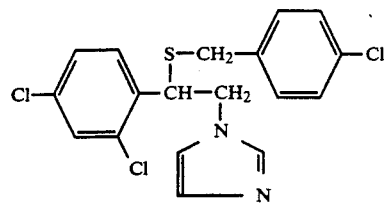

and is generally employed as the nitrate salt. It is commercially available as a 1% cream and 1% solution.

The present inventors have discovered that certain antifungal imidazole derivatives of the following formula I and dermatologically acceptable salts thereof, surprisingly and unexpectedly exhibit antiperspirant activity when topically applied in an antiperspirant effective amount to an area of mammalian skin subject to perspiration:

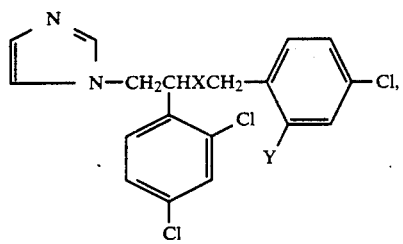

wherein X is O or S and Y is Cl or H

Preferred compounds of the formula I include: miconazole, econazole, sulconazole, and dermatologically acceptable salts thereof.

More preferred compounds of the formula I include: miconazole, econazole, and dermatologically acceptable salts thereof.

The most preferred compound of the formula I is miconazole and its dermatologically acceptable salts.

While acting to substantially prevent sweating, the imidazole derivatives of formula I, and their dermatologically acceptable salts, advantageously simultaneously act to prevent or cure fungal infections, such as candida or tinea, in the area of skin upon which they are applied.

The present inventors have been unable to find any reference in the literature to an antiperspirant effect of the imidazole derivatives of formula I or their dermatologically acceptable salts. Such effect is believed to be a new and surprising discovery.

The present invention is rendered even more surprising by the fact that imidazole itself possesses no antiperspirant activity.

The antiperspirant imidazole derivatives and dermatologically acceptable salts thereof in accordance with the present invention are applied to an area of the skin of a mammal, preferably a human, where perspiration occurs. Such areas include, for example, the axilla, the feet, the back, the chest, the hands, the crotch and the forehead. They are applied in an amount sufficient to elicit the desired antiperspirant effect. Generally they are applied by means of an antiperspirant composition containing from about 0.1% to about 1.5%, based on the total weight of the composition, of the antiperspirant imidazole derivative of formula I or dermatologically acceptable salt thereof. Preferably the concentration of the antiperspirant imidazole derivative of formula I, or the dermatologically acceptable salt thereof, is from about 0.25% to about 1.25%, based on the total weight of the composition; more preferably it is from about 0.5% to about 1%, based on the total weight of the composition; and most preferably it is about 0.5%.

The antiperspirant imidazole compounds and dermatologically acceptable salts thereof are desirably applied by incorporating same in a dermatologically acceptable vehicle. Suitable vehicles include emulsion based creams and lotions, powders, suspensions, aerosols, etc. Included within the present invention are compositions useful in the process of the invention.

As stated heretofore, topical compositions containing dermatologically acceptable salts of representative imidazoles of formula I, e.g. miconazole nitrate, econazole nitrate and sulconazole nitrate, are commercially available. Miconazole nitrate topical products contain 2% miconazole nitrate. Econazole nitrate and sulconazole nitrate topical products generally contain 1% of such actives.

Topical antiperspirant compositions of the present invention contain from about 0.1% to about 1.5%, based on the total weight of the composition, of the imidazole derivative of formula I, or a dermatologically acceptable salt thereof, in a compatible dermatologically acceptable vehicle or carrier. Preferably the compositions contain from about 0.25% to about 1.25% of the imidazole derivative of formula I or the dermatologically acceptable salt thereof. More preferably the compositions contain from about 0.5% to about 1% of the imidazole derivative of formula I or the dermatologically acceptable salt thereof. Most preferably the compositions contain about 0.5% of the imidazole derivative of formula I or the dermatologically acceptable salt thereof.

The amount of imidazole derivative of formula I or dermatologically acceptable salt thereof applied to the skin is greatly below the amounts utilized when miconazole, econazole and sulconazole are utilized as antifungals. Thus, the surprising and unexpected antiperspirant activity of these agents is made even more surprising and unexpected, by the low concentration at which these agents may be used for such purpose.

To demonstrate the antiperspirant activity of imidazole derivatives of formula I and their pharmaceutically acceptable salts, the following Modified Rat Foot Pad assay was employed:

Modified Rat Foot Pad Assay

The number of active sweat glands in the hind feet of a group of rats was established as a baseline.
Injection Studies The rats were then randomized into treatment groups based on these values. The test material was dissolved in 0.01 ml of normal saline and injected subcutaneously into foot pads containing the sweat glands. One foot was treated with the test material while the contralateral foot was treated with saline.
Topical Studies 5 microliters of test material were topically applied with the aid of a micropipette to foot pads while the contralateral feet were treated with the vehicle as a control. The change in the sweat ratio between the baseline and the treatment is indicative of the test materials' ability to inhibit sweat production.

EXAMPLE I

Utilizing the previously described assay procedure for Injection Studies, miconazole was injected in each of four pads of the treated foot, at a dose level of 1 or 10 micrograms per pad. Higher dose levels could not be used because of poor water solubility of the test compound. A total of four rats were treated with a dose of 10 micrograms per pad. A total of five rats were treated with a dose of 1 microgram per pad.

The test results of the Injection Studies are illustrated in the following Table I:

TABLE I

| Group | Animal # | Dose | % Inhibition | $\overline{X}$ | SE |
|---|---|---|---|---|---|
| A | 35295 | Hi | 46.0 | | |
| | 35296 | 10 μg/ | 29.4 | | |
| | 35301 | pad | 48.0 | 42.1 | 4.4 |
| | 35304 | | 45.0 | | |
| B | 35297 | Lo | 0 | | |
| | 35298 | 1 μg/ | 0 | | |
| | 35299 | pad | 11.0 | 3.0 | 2.1 |
| | 35302 | | 4.0 | | |
| | 35303 | | 0 | | |

As is evident from the results of Table I, the average sweat inhibition rate in the 1 microgram group was determined to be 3% (SE=2.1). The average sweat inhibition rate for the 10 micrograms group was determined to be 42.1% (SE=4.4).

EXAMPLE 2

Utilizing the previously described assay procedure for Topical Studies, miconazole and econazole were topically applied. The test results are illustrated in the following Table II:

TABLE II

| Test Materials | No. of Animals | % Inhibition $\overline{X}$ | SE |
|---|---|---|---|
| 0.5% Miconazole/Topical Base | 12 | 22.4 | 5.7 |
| 0.5% Econazole/Topical Base | 12 | 21.4 | 7.0 |
| 0.5% Miconazole/Ethanol | 6 | 16.2 | 16.8 |
| 0.5% Econzaole/Ethanol | 6 | 22.0 | 10.7 |

EXAMPLE 3

Using the previously described assay procedures for Injection Studies and for Topical Studies, sulconazole is evaluated. The test results show sulconazole has comparable antiperspirant activity to econazole.

What is claimed is:

1. A process for decreasing perspiration in an area of the skin subject to perspiration comprising applying to such area an amount effective to reduce perspiration, of an imidazole derivative of the formula I

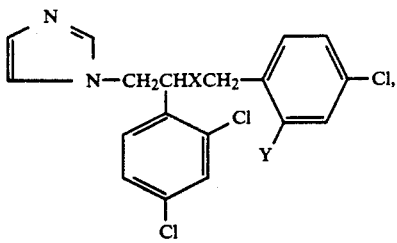

wherein X is O or S and Y is Cl or H, or a dermatologically acceptable salt thereof.

2. The process according to claim 1, wherein the compound formula I is selected from the group consisting of miconazole, econazole, sulconazole and dermatologically acceptable salts thereof.

3. The process according to claim 1, wherein the compound formula I is miconazole or a dermatologically acceptable salt thereof.

4. The process according to claim 1, wherein the compound formula I is econazole or a dermatologically acceptable salt thereof.

5. The process according to claim 1, wherein the compound formula I is sulconazole or a dermatologically acceptable salt thereof.

6. The process according to claim 1, wherein said area is in the axilla.

7. The process according to claim 1, wherein said area is on the forehead.

8. The process according to claim 1, wherein said area is on the foot.

9. The process according to claim 1, wherein said area is on the hand.

10. The process according to claim 1, wherein said area is in the crotch.

11. The process according to claim 1, wherein said area is on the back.

12. The process according to claim 1, wherein said area is the chest.

13. The process according to claim 1, wherein the imidazole derivative of formula I or a dermatologically acceptable salt thereof, is in a dermatologically acceptable carrier.

14. The process according to claim 13, wherein said carrier contains from about 0.1% to about 1.5% of the imidazole derivative of formula I or the dermatologically acceptable salt thereof is present in an amount of from about 0.1% to about 1.5%, based on total weight of the carrier and the imidazole derivative or salt thereof.

15. The process according to claim 14, wherein said carrier contains from about 0.25% to about 1.25% of the imidazole derivative of formula I or the dermatologically acceptable salt thereof is present.

16. The process according to claim 14, wherein from about 0.5% to about 1% of the imidazole derivative of formula I or the dermatologically acceptable salt thereof is present.

17. The process according to claim 14, wherein about 0.5% of the imidazole derivative of formula I or the dermatologically acceptable salt thereof is present.

18. A composition for decreasing perspiration comprising from about 0.1% to about 1.5%, based on the total weight of the composition, of an imidazole derivative of the formula I

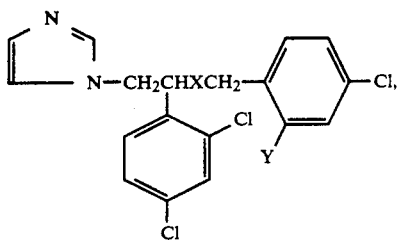

wherein X is O or S and Y is Cl or H, or a dermatologically acceptable salt thereof and from about 99.9% to about 98.5% of a compatible dermatologically acceptable carrier.

19. The composition according to claim 18, wherein the compound of formula I is miconazole or a dermatologically acceptable salt of miconazole.

20. The composition according to claim 18, wherein the compound of formula I is econazole or a dermatologically acceptable salt of econazole.

21. The composition according to claim 18, wherein the compound of formula I is sulconazole or a dermatologically acceptable salt of sulconazole.

22. The composition according to claim 18, wherein from about 0.25% to about 1.25% of the imidazole derivative of formula I or the dermatologically acceptable salt thereof is present.

23. The composition according to claim 18, wherein from about 0.5% to about 1% of the imidazole derivative of formula I or the dermatologically acceptable salt thereof is present.

24. The composition according to claim 18, wherein about 0.5% of the imidazole derivative of formula I or the dermatologically acceptable salt thereof is present.

* * * * *